United States Patent [19]

Drake et al.

[11] Patent Number: 4,866,097
[45] Date of Patent: Sep. 12, 1989

[54] CONTROLLED RELEASE SYSTEM

[75] Inventors: Cyril F. Drake, Harlow; Alfred J. Arch, Ongar, both of United Kingdom

[73] Assignee: Standard Telephones and Cables Public Limited Company (STC), Essex, United Kingdom

[21] Appl. No.: 647,754

[22] Filed: Sep. 6, 1984

[30] Foreign Application Priority Data

Sep. 15, 1983 [GB] United Kingdom ............ 8324785

[51] Int. Cl.⁴ ........................................... A61M 31/00
[52] U.S. Cl. ..................... 514/770; 514/964; 514/965; 71/1
[58] Field of Search ............ 514/770, 964, 965; 71/1; D24/63; D28/1, 5, 7

[56] References Cited

U.S. PATENT DOCUMENTS

| | | | |
|---|---|---|---|
| D. 103,976 | 4/1937 | Lermer | D24/63 |
| D. 185,734 | 7/1959 | Chappaz et al. | D24/63 |
| D. 199,606 | 11/1964 | Waterman | D24/63 |
| 1,991,345 | 2/1935 | Durand | D24/63 |
| 2,651,437 | 9/1953 | Fields | D24/63 |
| 3,369,543 | 2/1968 | Ronco | D24/63 |
| 3,944,064 | 3/1976 | Bashaw et al. | 424/14 |
| 3,946,734 | 3/1976 | Dedrick et al. | 604/891 |
| 3,962,414 | 6/1976 | Michaels | 424/14 |
| 4,014,675 | 3/1977 | Osburn | 71/1 |
| 4,203,442 | 5/1980 | Michaels | 424/19 |
| 4,449,981 | 5/1984 | Drake et al. | 604/890 |

FOREIGN PATENT DOCUMENTS

| | | |
|---|---|---|
| 2057420 | 4/1981 | United Kingdom . |
| 2077585 | 12/1981 | United Kingdom . |
| 2077586 | 12/1981 | United Kingdom . |
| 2111388 | 7/1983 | United Kingdom . |

Primary Examiner—Ronald W. Griffin
Attorney, Agent, or Firm—Kerkam, Stowell, Kondracki & Clarke

[57] ABSTRACT

A device for the controlled release of an active material into an aqueous medium comprises a water soluble capillary tube (11) the bore (12) of which contains an active material (13). Dissolution of the active material is diffusion limited during a delay period while the capillary is dissolving. When dissolution of the tube is complete rapid dissolution of the remaining active material then takes place.

18 Claims, 1 Drawing Sheet

CONTROLLED RELEASE SYSTEM

This invention relates to arrangements for providing the controlled release of an active material into an aqueous medium and to methods of manufacturing such compositions.

There is a broad range of applications wherein it is necessary to provide for the release of an active material at a controlled rate into an aqueous environment. In the biosciences, particularly, the potential for prolonging the action of numerous bioactive compounds is stimulating considerable interest. There is also the requirement for the release of the active material after an induction period, in the form of a single pulse or in the form of a series of pulses at predetermined intervals.

Since the early 1950's researchers have attempted to develop controlled release systems able to store active materials and then release them at contlrolled rates into aqueous systems. This research has tended to concentrate on polymeric materials. Many polymers may be fabricated at relatively low temperatures to encapsulate effectively active materials thereby protecting them from unwanted interaction with the environment. Subsequent release of the active material is effected by one of four general mechanisms, i.e. diffusion, swelling (bio), chemical action and magnetic processes. However, in most cases it has proved impractical to engineer the required degree of control, especially over long periods, and in many instances toxicity of the special polymer itself has limited exploitation.

Composite controlled release systems are known in which particulate soluble material dispersed in a significantly less soluble matrix are preferentially dissolved by a liquid medium to produce a network of capillaries through which an active material can then be released into solution. Typical of these systems are those described in our co-pending applications No. 2109665A (C. F. Drake-R. Jones 82-2) and No. 2111388A (C. F. Drake-R. Jones 83-3).

These types of controlled release systems suffer from the disadvantage that, if the particles of the soluble material are not each in contact with their neighbours then their continuous dissolution is interrupted by the inter-layer of less soluble matrix. This of course inhibits release of the active material to the liquid medium.

The object of the present invention is to minimise or to overcome this disadvantage.

According to the invention there is provided a device for the controlled release of a water soluble active material into an aqueous medium in contact with the device, the device including a water soluble capillary tube at least one end of which is open, which tube is filled with a composition comprising wholly or partially of the active material, wherein, when the device is contacted with an aqueous medium, dissolution of the active material takes place at a diffusion controlled rate until dissolution of the tube is complete allowing subsequent rapid release of the active material.

By providing a capillary tube of known dissolution rate and wall thickness delay period prior to rapid release of the active material can be adjusted to a devised value.

Advantageously the capillary tube is formed from a water soluble glass. Suitable glasses for this purpose include, but are not limited to, those described in our published specification No. 2057420A (C. F. Drake 70).

The term 'active material' as employed herein may include a medicament or therapeutic agent for use in human or animal treatment, a specific or non-specific biocidal material, a food, a food additive, a perfume, a pheromone, a fertiliser of a selective or non-selective herbicide. Other materials include a water-snail attractant/poison, an insecticide, and materials selected to release inorganic substances for biological or non-biological applications. Further materials include radiosensitising drugs for radio-therapy applications. In some applications the capillary itself may include an inorganic material which becomes active when dissolved in solution. This material may be provided in the form of a metal oxide.

An embodiment of the invention will now be described with reference to the accompanying drawings in which.

Figure 1:
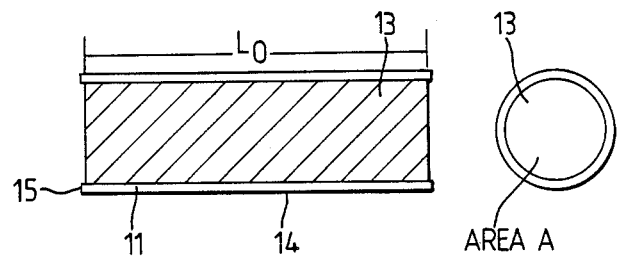
FIG. 1 is a sectional view of the controlled release device.

Referring to FIG. 1, the device comprises a capillary tube 11 made of a water soluble material, e.g. a glass composition, the bore of which is filled with a composition 13 consisting wholly or partially of an active material. The bore of the capillary is of sufficiently small diameter that, prior to dissolution of the tube, the dissolution rate of the composition 13 is limited by the rate at which it can diffuse to the mouth of the bore.

When the device is placed in an aqueous medium the capillary tube 11 dissolves both from its exterior walls 14 and from its end surface 15. If the thickness of the tube is small relative to its length then the rate determining process will be dissolution of the wall 14 of the tube to expose the composition 13. When dissolution of the tube is complete (i.e., dissolution through the wall 14) the dissolution rate of the composition 13 to release the active material is no longer diffusion limited and rapid release is therefore effected.

Figure 2:
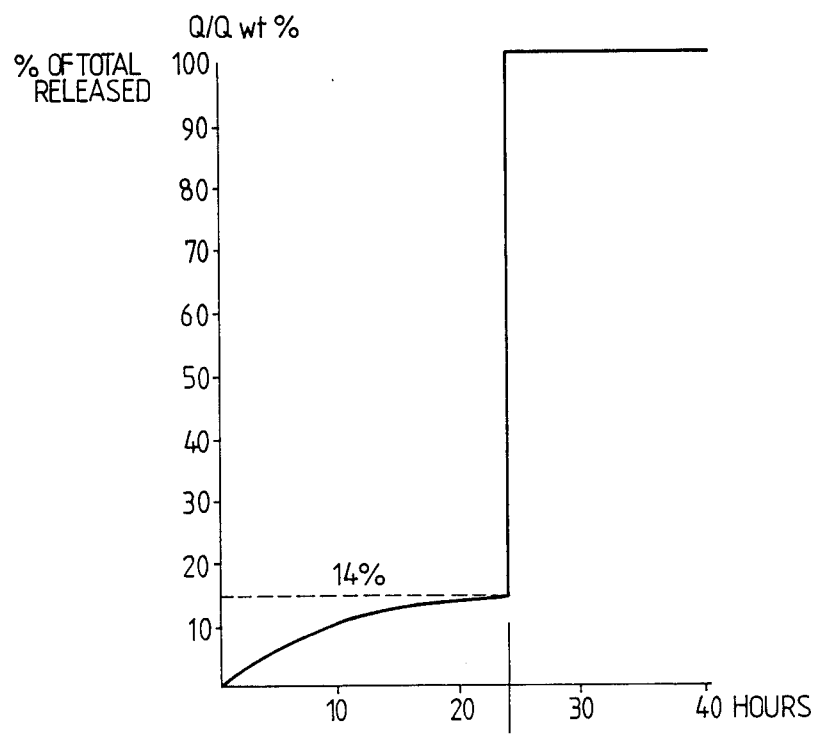
FIG. 2 shows a typical release rate/time characteristic of the device of FIG. 1.

Prior to dissolution of the capillary, the rate of diffusion of the active material from the tube ends is proportional to the square root of time. During this phase of the dissolution process the release rate of active material thus steadily decreases and in fact represent only a small proportion of the total amount of active material in the capillary. This effect is illustrated in FIG. 2 where it can be seen that during the initial delay period, in this case 24 hours, very little release of active material is effected. At the end of this delay period release of the remaining active material is substantially instantaneous.

When the filled capillary is immersed in water the filler material 13 dissolves from its open ends. Initially rapid dissolution is effected but once the solid/liquid boundary has retreated a small distance into the capillary bore the dissolution rate is limited by the diffusion of active material from the bore. This of course is a relatively slow process the rate of which is given by the expression $$Q = A(2DC\rho t)^{\frac{1}{2}}$$

where Q is the total mass in grammes of active material dissolved, t is the time in days, D is the diffusion coefficient of the active material in the aqueous medium, $\rho$ is the density of the material and A is the cross-sectional area of the capillary.

The length $X_A$ of the column of the material dissolved after time t is given by $$X_A = (2DCt)^{\frac{1}{2}}$$

For a typical value of the diffusion coefficient of a moderate molecular weight material in water at room temperature, $D \simeq 0.2$ cm$^2$d$^{-1}$ and taking $\rho = 1$ and $C = 1$ g/l we have $$X_A = 2 \times 10^{-2} \cdot t^{\frac{1}{2}}$$

Thus, in this example, the length of active material dissolved in one day is 0.2 mm and in 100 days 2 mm.

As previously stated the delay period prior to release of the major proportion of the active material is determined by the wall thickness and dissolution rate of the capillary tube 11. The relatively simple calculation involved will be apparent to those skilled in the art.

We prefer to employ a water soluble glass from the fabrication of the capillary tube 11. Typically we employ glasses including phosphorous pentoxide as the principal glass forming oxide metal and alkali metal plus alkaline earth metal oxides as the glass modifying components. The glass may also include alumina as a further glass modifying oxide. The dissolution rate of such a glass can be controlled by adjustment of the relative proportion of these oxides. For example the dissolution rate may be increased by increasing the proportion of an alkali metal oxide and decreased by the addition of alumina. The techniques of glas dissolution rate control are more fully described in our published specification No. 2,057,420A. The glass may also contain one or more metals in oxide form which on dissolution themselves provide active materials.

The glass is fused and drawn into a capillary tube by conventional techniques. Lengths of this tube are then filled with the composition containing or comprising the active material by capillary absorption of the material in liquid form either as a melt or as a solution in a suitable solvent.

The following example illustrates the invention:

A glass was prepared by melting a batch comprising:

| mole % | | | |
|---|---|---|---|
| NaH$_2$PO$_4$ | 27.0 | 22.5 | Na$_2$O |
| CaHPO$_4$ | 22.1 | 32.5 | CaO |
| P$_2$O$_5$ | 5.0 | 45.0 | P$_2$O$_5$ | for 1 h in a platinum crucible at 115° C.

The glass was cast into large diameter cylinders and drawn to a capillary with a bore of 0.3 mm and a wall thickness of 0.3 mm. A 2 cm length of the tubing was filled by capillary action with molten benzoic acid and allowed to cool. The multant controlled-delay delivery device was placed in water at 38° C. and after 29 days the wall of the capillary had dissolved through to release the benzoic acid.

It will be clear that the delay time could be readily charged by using a glass of a different composition and that the benzoic acid used as a 'model' material could be replaced by an action agent, for example an helminticide.

It will also be clear that a 'package' of a number of tubes with different wall thicknesses or different compositions would provide a device which delivered pulses of the contained material at predetermined intervals.

We claim:

1. A device having two controlled release rates of a water soluble active material into an aqueous medium in contact with the device, the device including a water soluble capillary tube having a wall and at least one open end, said tube being filled with a composition comprised wholly or partially of the active material, wherein, when the device is contracted with an aqueous medium, dissolution of the active material takes place at a first diffusion controlled rate with diffusion at least through said at least one open end until dissolution through the wall, thereafter the active material is released at a second rapid release rate, there being a sufficient amount of the composition relative to the first diffusion controlled rate and the time required for dissolution of the wall that a portion of the composition is not released until dissolution through the wall.

2. A device as claimed in claim 1, wherein the capillary tube comprises a water soluble glass.

3. A device as claimed in claim 2, wherein the tube comprises a phosphate glass.

4. A device as claimed in claim 1, wherein the active material is a medicament or therapeutic agent.

5. A device as claimed in claim 1, wherein the active material includes a mixture of a water snail attractant and a poison.

6. A device as claimed in claim 1, wherein the active material is a radiosensitizing drug.

7. A device as claimed in claim 1, wherein the active material is a herbicide or insecticide.

8. A device as claimed in claim 1, wherein the capillary tube incorporates a further active material released on dissolution through the wall.

9. A device as claimed in claim 2, wherein the active material is a medicament or therapeutic agent.

10. A device as claimed in claim 2, wherein the active material includes a mixture of a water snail attractant and a poison.

11. A device as claimed in claim 2 wherein the active material is a radiosensitizing drug.

12. A device as claimed in claim 2 wherein the active material is a herbicide or insecticide.

13. A device as claimed in claim 3, wherein the active material is a medicament or therapeutic agent.

14. A device as claimed in claim 3, wherein the active material includes a mixture of a water snail attractant and a poison.

15. A device as claimed in claim 3 wherein the active material is a radiosensitizing drug.

16. A device as claimed in claim 3 wherein the active material is a herbicide or insecticide.

17. The device as claimed in claim 1 wherein said tube has two open ends and the first diffusion controlled rate involves diffusion through both open ends.

18. A method for releasing water soluble active material into an aqueous medium at two controlled release rates, the steps comprising:
    making a device having a water soluble capillary tube with a wall and with at least one open end, the tube being filled with a composition comprised wholly or partially of the active material; and
    placing said device in contact with an aqueous medium such that dissolution of the active material takes place at a first diffusion controlled rate at least through the at least one open end until dissolution through the wall and, upon dissolution of the wall, there is remaining active material which is released at a second rapid release rate.

* * * * *